United States Patent

Junino et al.

[11] Patent Number: 5,609,649
[45] Date of Patent: Mar. 11, 1997

[54] TINCTORIAL COMPOSITION FOR KERATINOUS FIBERS CONTAINING OXIDATION DYE PRECURSORS AND COUPLERS DERIVED FROM 4-HYDROXYINDOLE, AND DYEING METHOD USING THEM

[75] Inventors: Alex Junino, Livry-Gargan; Jean J. Vandenbossche, Aulnay-sous-Bois; Herve Richard, Paris; Jean Cotteret, Verneuil-sur-Seine, all of France

[73] Assignee: L'Oreal, Paris, France

[21] Appl. No.: 262,444

[22] Filed: Jun. 20, 1994

Related U.S. Application Data

[63] Continuation of Ser. No. 933,937, Aug. 24, 1992, abandoned, which is a continuation of Ser. No. 611,139, Nov. 9, 1990, abandoned.

[30] Foreign Application Priority Data

Nov. 10, 1989 [FR] France ................................. 8914794

[51] Int. Cl.$^6$ ..................................................... A61K 7/13
[52] U.S. Cl. ........................... 8/409; 8/406; 8/407; 8/408; 8/410; 8/411; 8/412; 8/423
[58] Field of Search ................................ 8/405, 406, 407, 8/408, 412, 414, 416, 423, 409, 410, 411

[56] References Cited

U.S. PATENT DOCUMENTS

| 4,013,404 | 3/1977 | Parent et al. ................................. 8/11 |
| 5,034,015 | 7/1991 | Junino et al. ............................... 8/423 |
| 5,131,911 | 7/1992 | Lang et al. .................................. 8/410 |

FOREIGN PATENT DOCUMENTS

| 0271186 | 6/1988 | European Pat. Off. . |
| 0360638 | 3/1990 | European Pat. Off. . |
| 2636235 | 3/1990 | France . |
| 2636237 | 3/1990 | France . |
| 3031709 | 4/1982 | Germany . |

OTHER PUBLICATIONS

English Language Translation of DE, 3,031,709, Wella AG, Apr. 22, 1982, pp. 1–12.

*Primary Examiner*—Paul Lieberman
*Assistant Examiner*—Caroline L. Dusheck
*Attorney, Agent, or Firm*—Cushman Darby & Cushman Intellectual Property Group of Pillsbury Madison & Sutro LLP

[57] ABSTRACT

Tinctorial composition for keratinous fibers, in particular for human hair, characterized in that it contains, in a medium appropriate for dyeing these fibers, at least one para oxidation dye precursor or at least one ortho oxidation dye precursor in combination with at least one heterocyclic coupler, corresponding to the formula:

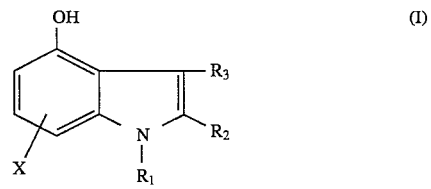

in which $R_1$ denotes a hydrogen atom or a $C_1$–$C_4$ alkyl radical; $R_2$ denotes a hydrogen atom, a $C_1$–$C_4$ lower alkyl radical, a carboxyl radical or an alkoxycarbonyl radical; $R_3$ denotes a hydrogen or halogen atom, a $C_1$–$C_4$ lower alkyl radical, a carboxyl radical, an alkoxycarbonyl radical or a formyl radical; X denotes a hydrogen atom, a $C_1$–$C_4$ alkyl radical, a halogen atom, a $C_1$–$C_4$ alkoxy radical, an acetylamino group or a dialkyl($C_1$–$C_4$)aminomethyl group; at least one of the groups X, $R_1$, $R_2$ and $R_3$ differing from hydrogen; as well as their salts.

21 Claims, No Drawings

TINCTORIAL COMPOSITION FOR KERATINOUS FIBERS CONTAINING OXIDATION DYE PRECURSORS AND COUPLERS DERIVED FROM 4-HYDROXYINDOLE, AND DYEING METHOD USING THEM

This is a continuation of application Ser. No. 07/933,937, filed Aug. 24, 1992, now abandoned which is a continuation of application Ser. No. 07/611,139 filed Nov. 9, 1990, now abandoned.

The present invention relates to new tinctorial compositions for keratinous fibers and in particular for human hair, containing oxidation dye precursors and couplers derived from 4-hydroxyindole, and to dyeing methods using such compositions.

It is known to dye keratinous fibers, and in particular human hair, with tinctorial compositions containing oxidation dye precursors and in particular p-phenylenediamines or ortho- or para-aminophenols, which are generally termed "oxidation bases".

It is also known that the hues obtained with these oxidation bases can be varied by combining them with couplers, also termed coloring modifiers, such as aromatic metadiamines, meta-aminophenols and metadiphenols.

In the field of hair dyeing, oxidation dye precursors or couplers are sought which enable a coloring having a satisfactory resistance to light, to washing, to the weather and to perspiration to be imparted to the hair, in an oxidizing alkaline medium generally used in oxidation dyeing.

The applicants have just discovered, and it is this which is the subject of the invention, that certain 4-hydroxyindole derivatives as couplers, with oxidation dye precursors of para or ortho type, enabled dyeings having particularly surprising resistance to light, to washing, to the weather and to perspiration to be obtained after application to the keratinous fibers and in particular the hair, in particular when these couplers are used with p-phenylenediamine and its derivatives.

One subject of the invention therefore comprises oxidation tinctorial compositions, intended to be used for dyeing keratinous fibers, containing at least one oxidation dye precursor of the para and/or ortho type with 4-hydroxyindole derivatives.

Another subject of the invention comprises the method for coloring keratinous fibers, in particular human hair, using such a composition.

Further subjects of the invention will become apparent on reading the description and the examples which follow.

The oxidation tinctorial composition according to the invention, intended to be used for dyeing keratinous fibers and in particular human hair, is essentially characterized in that it contains, in a medium appropriate for dyeing, at least one para and/or ortho oxidation dye precursor and at least one heterocyclic coupler, corresponding to the formula (I):

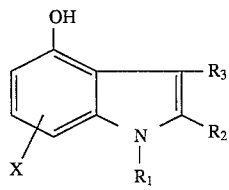

in which $R_1$ denotes a hydrogen atom or a $C_1$–$C_4$ alkyl radical; $R_2$ denotes a hydrogen atom, a $C_1$–$C_4$ lower alkyl radical, a carboxyl radical or an alkoxycarbonyl radical; $R_3$ denotes a hydrogen or halogen atom, a $C_1$–$C_4$ lower alkyl radical, a carboxyl radical, an alkoxycarbonyl radical or a formyl radical; X denotes a hydrogen atom, a $C_1$–$C_4$ alkyl radical, a halogen atom, a $C_1$–$C_4$ alkoxy radical, an acetylamino radical or a dialkyl($C_1$–$C_4$)aminomethyl radical; at least one of the groups X, $R_1$, $R_2$ and $R_3$ differing from hydrogen; as well as their salts.

Amongst the compounds of formula (I), the particularly preferred compounds are those in which the alkyl radical denotes methyl or ethyl and the alkoxycarbonyl radical denotes methoxycarbonyl or ethoxycarbonyl.

Amongst these compounds, those which may be mentioned are 4-hydroxy-5-ethoxyindole, 4-hydroxy-5-methoxyindole, 4-hydroxy-1-methyl-5-ethoxyindole, 4-hydroxy-2-ethoxycarbonyl-5-ethoxyindole, 4-hydroxy-2-methyl-5-ethoxyindole, 4-hydroxy-7-methoxy-2,3-dimethylindole, 4-hydroxy-5-methylindole, 4-hydroxy-3-chloroindole, 4-hydroxy-5-dimethylaminomethylindole, 4-hydroxy-3-formyl-2-methyl-1-ethylindole, 4-hydroxy-3-formylindole, 4-hydroxy-3-formyl-2,6-dimethylindole, 4-hydroxy-3-formyl-1-methylindole, 4-hydroxy-2-methyl-5-ethoxyindole, 4-hydroxy-1,5-dimethylindole, 4-hydroxy-5-methyl-2-carboxyindole, 4-hydroxy-6-methyl-3-ethoxycarbonylindole, 4-hydroxy-7-methylindole, 4-hydroxy-2,5-dimethyl-1-ethylindole, 4-hydroxy-2,6-dimethyl-1-ethylindole, 4-hydroxy-2-methyl-1-ethylindole, 4-hydroxy-3-ethylindole, 4-hydroxy-2,6-dimethylindole, 4-hydroxy-6-methylindole and 4-hydroxy-2-carboxy-5-methylindole.

4-Hydroxy-1,5-dimethylindole and 4-hydroxy-2-carboxy-5-methylindole are new and constitute another subject of the invention.

The dye precursors of para or ortho type are compounds which are not themselves dyes but which form a dye by an oxidative condensation process, either on themselves or in the presence of a coupler or modifier.

These compounds contain functional groups, these being either two amino or one amino and one hydroxyl, in the para or ortho position, the one relative to the other.

The precursors of para type are chosen from paraphenylenediamines, para-aminophenols, para heterocyclic precursors, such as 2,5-diaminopyridine, 2-hydroxy-5-aminopyridine and tetraaminopyrimidine and the so-called "double" bases.

Paraphenylenediamines which may be mentioned are the compounds corresponding to the formula (II) below:

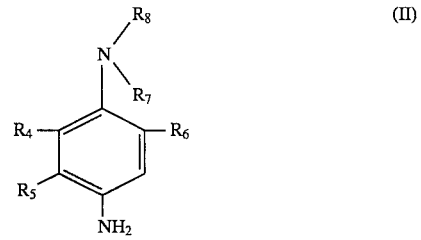

in which $R_4$, $R_5$ and $R_6$, which may be identical or different, represent a hydrogen or halogen atom, an alkyl radical having 1 to 4 carbon atoms or an alkoxy radical having 1 to 4 carbon atoms, and $R_7$ and $R_8$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl or morpholinoalkyl radical, these alkyl or alkoxy groups having from 1 to 4 carbon atoms, or $R_7$ and $R_8$ form, together with the nitrogen atom to which they are bonded, a piperidino or morpholino heterocycle, with the proviso that $R_4$ or $R_6$ represents a hydrogen atom when $R_7$ and $R_8$ do not represent a hydrogen atom, as well as the salts of these compounds.

Amongst the compounds of formula (II), the following may be mentioned more particularly: p-phenylenediamine, p-toluylenediamine, methoxyparaphenylenediamine, chloroparaphenylenediamine, 2,6-dimethylparaphenylenediamine, 2,5-dimethylparaphenylenediamine, 2-methyl-5-methoxyparaphenylenediamine, 2,6-dimethyl-5-methoxyparaphenylenediamine, N,N-dimethylparaphenylenediamine, 3-methyl-4-amino-N,N-diethylaniline, N,N-di(β-hydroxyethyl)paraphenylenediamine, 3-methyl-4-amino-N,N-di-(β-hydroxyethyl)aniline, 3-chloro-4-amino-N,N-di-(β-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl,β-piperidinoethyl)aniline, 3-methyl-4-amino-N,N-(ethyl,β-piperidinoethyl)aniline, 4-amino-N,N-(ethyl,β-morpholinoethyl)aniline, 3-methyl-4-amino-N,N-(ethyl,β-morpholinoethyl)aniline, 4-amino-N,N-(ethyl,β-acetylaminoethyl)aniline, 4-amino-N-(β-methoxyethyl)aniline, 3-methyl-4-amino-N,N-(ethyl,β-acetylaminoethyl)aniline, 4-amino-N,N-(ethyl,β-mesylaminoethyl)aniline, 3-methyl-4-amino-N,N-(ethyl,β-mesylaminoethyl)aniline, 4-amino-N,N-(ethyl,β-sulphoethyl)aniline, 3-methyl-4-amino-N,N-(ethyl,β-sulphoethyl)aniline, N-[(4'-amino)phenyl]morpholine and N-[(4'-amino)phenyl]piperidine.

These oxidation dye precursors of para type can be introduced into the tinctorial composition either in the form of the free base or in the form of salts, such as in the form of the hydrochloride, hydrobromide or sulphate.

Amongst the p-aminophenols, the following may be mentioned: p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

The oxidation dye precursors of ortho type are chosen from ortho-aminophenols, such as 1-amino-2-hydroxybenzene, 6-methyl-1-hydroxy-2-aminobenzene and 4-methyl-1-amino-2-hydroxybenzene, and orthophenylenediamines.

The so-called double bases are bis-phenylalkylenediamines corresponding to the formula:

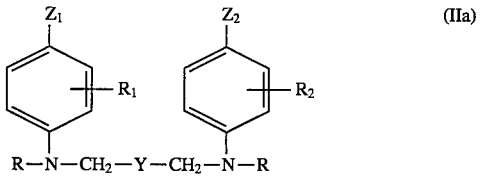

(IIa)

in which:

$Z_1$ and $Z_2$, which may be identical or different, represent hydroxyl or $NHR_3$ groups, where $R_3$ denotes a hydrogen atom or a lower alkyl radical;

$R_1$ and $R_2$, which may be identical or different, represent either hydrogen atoms or halogen atoms or alkyl groups;

R represents a hydrogen atom or an alkyl, hydroxyalkyl or aminoalkyl group, in which the amino radical can be substituted; and Y represents a radical taken from the group comprising the following radicals: $-(CH_2)_n-$, $-(CH_2)_n-O-(CH_2)_n-$, $-(CH_2)_n-$, $-CHOH-(CH_2)_n-$, $-(CH_2)_n-$

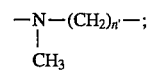

n being an integer between 0 and 8 and n' being an integer between 0 and 4, it being possible for this base to be in the form of its addition salts with acids.

The alkyl or alkoxy radicals preferably denote a group having 1 to 4 carbon atoms and in particular methyl, ethyl or propyl or methoxy or ethoxy.

Amongst the compounds of formula (IIa), the following may be mentioned: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine.

In addition to the heterocyclic coupler from the family of 4-hydroxyindoles of formula (I) defined above, the tinctorial compositions may also contain other couplers known per se, such as metadiphenols, meta-aminophenols, metaphenylenediamines, meta-acylaminophenols, meta-ureidophenols, metacarbalkoxyaminophenols, α-naphthol, 4-hydroxyindole and couplers having an active methylene group, such as the β-keto compounds and pyrazolones.

Amongst these couplers, the following may be mentioned more particularly: 2,4-dihydroxyphenoxyethanol, 2,4-dihydroxyanisole, meta-aminophenol, resorcinol monomethyl ether, 2-methyl-5-N-(β-hydroxy-ethyl)-aminophenol, 2-methyl-5-N-(β-mesylaminoethyl)aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]-phenoxyethanol, 2-amino-4-N-(β-hydroxyethyl)aminoanisole, 2,4-diaminophenyl β,γ-dihydroxypropyl ether, 2,4-diaminophenoxyethylamine, 2-methyl-5-aminophenol and 2,6-dimethyl-3-aminophenol and their salts.

As is well known in the state of the art, direct dyes, such as azo or anthraquinone dyes or the nitro derivatives of the benzene series, may be added to these compositions, in particular with a view to shading, or enriching with glints, the colorings imparted by the oxidation dye precursors and the coupler of formula (I).

These compositions do not contain any quinone derivative of the family of benzoquinones or naphthoquinones which is capable of oxidizing the 4-hydroxyindole derivative.

The compositions contain neither iodide nor nitrite ions present in amounts capable of oxidizing the oxidation dye precursors and the heterocyclic coupler. This exclusion does not exclude the possibility of using water containing, in the natural state, this type of ions in the form of traces.

The oxidation dye precursors of para and/or ortho type and the couplers used in the tinctorial compositions according to the invention preferably represent, as a whole, from 0.3 to 7% by weight relative to the weight of the said composition. The concentration of compounds (I) may vary between 0.05 and 3.5% by weight relative to the total weight of the composition.

The medium appropriate for dyeing is generally an aqueous medium and its pH may vary between 8 and 11 and is preferably between 9 and 11.

It is adjusted to the desired value with the aid of an alkalinizing agent, such as ammonia, alkali metal carbonates and alkanolamines, such as mono-, di- or tri-ethanolamine.

The tinctorial compositions according to the invention also contain, in their preferred embodiment, anionic, cationic, nonionic or amphoteric surfactants or their mixtures. Amongst these surfactants, the following may be mentioned: fatty alcohol alkylbenzenesulphonates, alkylnaphthalenesulphonates, sulphates, ether-sulphates and sulphonates, quaternary ammonium salts, such as trimethylcetylammonium bromide and cetylpyridinium bromide, optionally oxyethylenated fatty acid ethanolamides; polyoxyethylenated acids, alcohols or amines, polyglycerolated alcohols, polyoxyethylenated or polyglycerolated alkylphenols and polyoxyethylenated alkyl sulphates.

These surfactants are present in the compositions according to the invention in proportions of between 0.5 and 55% by weight, and preferably between 2 and 50% by weight, relative to the total weight of the composition.

These compositions may also contain organic solvents to dissolve the compounds which would not be sufficiently soluble in water. Amongst these solvents, the following may be mentioned by way of example: $C_1$–$C_4$ lower alkanols, such as ethanol and isopropanol; glycerol; glycols or glycol ethers, such as 2-butoxyethanol, ethylene glycol, propylene glycol and diethylene glycol monoethyl ether and monomethyl ether, and also aromatic alcohols, such as benzyl alcohol or phenoxyethanol and the analogous products or their mixtures.

The solvents are preferably present in proportions of between 1 and 40% by weight and in particular between 5 and 30% by weight, relative to the total weight of the composition.

The thickeners which may be added to the compositions according to the invention may be chosen in particular from sodium alginate, gum arabic, cellulose derivatives, acrylic acid polymers and xanthan gum. Inorganic thickeners may also be used, such as bentonite.

These thickeners are preferably present in proportions of between 0.1 and 5% and in particular between 0.2 and 3% by weight, relative to the total weight of the composition.

The antioxidants which may be present in the compositions are chosen, in particular, from sodium sulphite, thioglycolic acid, sodium bisulphite, ascorbic acid, hydroquinone and homogentisic acid. These antioxidants are present in the composition in proportions of between 0.05 and 1.5% by weight, relative to the total weight of the composition.

These compositions may also contain other cosmetically acceptable adjuvants, such as, for example, penetration agents, sequestering agents, perfumes, buffers, etc.

The compositions according to the invention may be in various forms, such as in the form of liquids, creams or gels or in any other form appropriate for effecting a dyeing of keratinous fibers and in particular of human hair. These compositions may be packaged in aerosol bottles in the presence of a propellant.

The tinctorial compositions according to the invention containing an oxidation dye precursor of the para and/or ortho type and a coupler of formula (I) are used in the methods for dyeing keratinous fibers and in particular human hair, in accordance with a method using development by an oxidizing agent.

In accordance with this method, the tinctorial composition described above is mixed, at the time of use, with an oxidizing solution in an amount sufficient to be able to develop a coloring and the mixture obtained is then applied to the keratinous fibers and in particular human hair.

The oxidizing solution contains, as oxidizing agent, hydrogen peroxide, urea peroxide or per salts, such as ammonium persulphate. A 20 volume hydrogen peroxide solution is preferably used.

The mixture obtained is applied to the hair and is left on the hair for 10 to 40 minutes, preferably 15 to 30 minutes, after which the hair is rinsed, washed with shampoo, rinsed again and dried.

The heterocyclic coupler of formula (I) defined above may also be used in a multi-step method consisting, in one of the steps, in applying the para and/or ortho oxidation dye precursor and, in another step, in applying the coupler of formula (I).

The oxidizing agent can be introduced just before the application, into the composition applied in the second step or can be added to the keratinous fibers themselves in a third step, the conditions for exposure and drying or washing being identical.

The examples which follow are intended to illustrate the invention without any limitation being implied.

In the examples, the following composition is prepared:

| COMPOSITION A | |
|---|---|
| Dyes | x g |
| Octyldodecanol sold under the name "EUTANOL G ®" by Henkel | 8.0 g |
| Oleic acid | 20.0 g |
| Monoethanolamine lauryl ether sulphate sold under the name "SIPON LM 35 ®" by Henkel | 3.0 g |
| Ethyl alcohol | 10.0 g |
| Benzyl alcohol | 10.0 g |
| Cetylstearyl alcohol containing 33 moles of ethylene oxide, sold under the name "SIMULSOL GS ®" by Seppic | 2.4 g |
| Ethylenediaminetetraacetic acid | 0.2 g |
| Cationic polymer consisting of recurring units: | 2.2 g |

$$\left[ \begin{array}{cc} CH_3 & CH_3 \\ | & | \\ {}^{\oplus}N-(CH_2)_3- & {}^{\oplus}N-(CH_2)_6 \\ | & | \\ CH_2\ Cl^{\ominus} & CH_3\ Cl^{\ominus} \end{array} \right]$$

| | |
|---|---|
| Monoethanolamine | 7.5 g |
| Linoleic acid diethanolamide sold under the name "COMPERLAN F ®" by Henkel | 8.0 g |
| Ammonia containing 20% $NH_3$ | 10.2 g |
| 35% aqueous sodium metabisulphite solution | 1.3 g |
| Hydroquinone | 0.15 g |
| 1-Phenyl-3-methyl-5-pyrazolone | 0.20 g |
| Demineralized water | qs 100.0 g |

| dyes | x g |
|---|---|
| polyglycerolated oleyl alcohol containing 2 moles of glycerol | 4.5 g |
| polyglycerolated oleyl alcohol containing 4 moles of glycerol | 4.5 g |
| "ETHOMEEN O12 ®" - Armoon Hess Chemical Ltd. (oxyethylenated oleylamine containing 12 moles of E.O.) | 4.5 g |
| "COMPERLAN KD ®" - Henkel (copra diethanolamide) | 9 g |
| propylene glycol | 4 g |
| 2-butoxyethanol | 8 g |
| 96° ethanol | 6 g |
| "MASQUOL DTPA ®" - Protex (pentasodium salt of diethylenetriaminepentaacetic acid) | 2 g |
| hydroquinone | 0.15 g |
| 35° Bé sodium bisulphite solution | 1.3 g |
| 22° Bé ammonia | 10 g |
| water | qs 100 g |

The dyes indicated in the table which follows are introduced in the amounts mentioned.

Composition A is used in Examples 1 to 10. Composition B is used in Examples 11 to 17.

These compositions are mixed, respectively, weight for weight with an oxidizing composition assaying 20 volume hydrogen peroxide and having a pH of 3.

The mixtures thus produced are applied for 30 minutes to grey hair which is 90% white for Examples 1 to 13 and 15 to 17, and to bleached hair for Example 14, and the hair is then rinsed and washed with shampoo and rinsed again and then dried.

The colorings shown in the table are those found after drying.

ml), toluene (7 ml) and tetrabutylammonium hydrogen sulphate (280 mg) are introduced successively.

The mixture is heated to 60° C. and dimethyl sulphate (1.2 ml) is introduced. The mixture is left at 60° C. for 30 minutes and diluted with water and the two phases are separated.

The organic phase is washed with water and dried and the solvent is evaporated.

TABLE I

| Examples | Heterocyclic coupler of formula (I) | g | Para precursor | g | Color |
|---|---|---|---|---|---|
| 1 | 2,3-dimethyl-4-hydroxy-7-methoxyindole | 0.382 | p-phenylenediamine | 0.216 | light ash beige blonde |
| 2 | 2,3-dimethyl-4-hydroxy-7-methoxyindole | 0.764 | p-aminophenol | 0.436 | golden iridescent blonde |
| 3 | 4-hydroxy-5-methoxyindole | 0.652 | p-aminophenol | 0.436 | ash beige blonde |
| 4 | 4-hydroxy-5-methylindole | 0.32 | p-phenylenediamine | 0.216 | dark purple |
| 5 | 4-hydroxy-5-methylindole | 0.65 | p-aminophenol | 0.436 | coppery red |
| 6 | 4-hydroxy-5-methoxy-2-methylindole | 0.32 | p-phenylenediamine | 0.216 | light ash blonde |
| 7 | 4-hydroxy-5-ethoxy-2-methylindole | 0.75 | p-aminophenool | 0.436 | ash blonde |

TABLE II

| Examples | Heterocyclic coupler of formula (I) | g | Para precursor | g | Color |
|---|---|---|---|---|---|
| 8 | 4-hydroxy-5-ethoxy 2-ethoxycarbonyl-indole | 0.354 | p-phenylene-diamine | 0.216 | iridescent light ash blonde |
| 9 | 4-hydroxy-5-ethoxy-2-ethoxycarbonyl-indole | 0.708 | p-phenylene-diamine | 0.436 | iridescent coppery light blonde |
| 10 | 4-hydroxy-2-methyl-5-ethoxyindole | 0.76 | p-aminophenol | 0.436 | golden beige light blonde |
| 11 | 1-methyl-5-ethoxy-4-hydroxyindole | 0.478 | p-aminophenol | 0.272 | orangey beige |
| 12 | 4-hydroxy-5-methyl-indole | 0.368 | p-aminophenol | 0.272 | orange-coloured |
| 13 | 4-hydroxy-5-methyl-indole | 0.362 | p-phenylene-diamine | 0.270 | purplish chestnut |
| 14 | 4-hydroxy-5-(dimethyl aminomethyl)indole | 0.475 | p-phenylene-diamine | 0.270 | bluish black |
| 15 | 4-hydroxy-3-formyl-indole | 0.403 | p-phenylene-diamine | 0.270 | ash chestnut |
| 16 | 4-hydroxy-3-formyl-indole | 0.403 | p-aminophenol | 0.872 | slightly golden beige |
| 17 | 4-hydroxy-5-methyl-2-carboxyindole | 0.478 | p-phenylene-diamine | 0.270 | purplish grey |

PREPARATION EXAMPLES

Example 1: Preparation of 1,5-dimethyl-4-hydroxyindole a) Preparation of 4-benzyloxy-1,5-dimethylindole 4-Benzyloxy-5-methylindole obtained by the method of F. Troxler et al. Helvetica Chimica Acta, 51, 1203 (1968) (2.5 g, 0.0105 mol), 50% sodium hydroxide solution (12

A pale green oil is obtained. After chromatography on silica (eluent: $CH_2Cl_2$/heptane 50:50), a colorless oil of 4-benzyloxy-1,5-dimethylindole (1.9 g) is obtained.

Yield=72%. Analysis: $C_{17}H_{17}NO$

|  | C | H | N | O |
|---|---|---|---|---|
| Calculated: | 81.24 | 6.82 | 5.57 | 6.37 |
| Found: | 81.06 | 6.88 | 5.45 | 6.28 | b) Preparation of 1,5-dimethyl-4-hydroxyindole

A mixture of the above derivative (1.8 g, 0.0072 mol), cyclohexene (2.5 ml), absolute ethanol (15 ml) and palladium-on-charcoal (0.4 g) is refluxed for 3 hours.

The mixture is filtered hot and the solvent is evaporated.

After passing through a silica column (eluent $CH_2Cl_2$), a crushed white powder of 1,5-dimethyl-4-hydroxyindole (0.5 g) is obtained.

Yield=44%, m.p.=68° C. Analysis: $C_{10}H_{11}NO$

|  | C | H | N | O |
|---|---|---|---|---|
| Calculated: | 74.51 | 6.88 | 8.69 | 9.92 |
| Found: | 74.48 | 6.90 | 8.72 | 10.10 |

Example 2: Preparation of 2-carboxy-4-hydroxy-5-methylindole

4-Benzyloxy-2-carboxy-5-methylindole obtained by the method of F. TROXLER et al. Helvetica Chimica Acta, 51, 1203 (1968) (0.8 g, 2.84 $10^{-3}$ mol), cyclohexene (1.5 ml), absolute ethanol (8 ml) and palladium-on-charcoal (0.2 g) are introduced successively.

The mixture is refluxed for 2 hours. The mixture is filtered hot, the material on the filter is rinsed copiously with hot methanol and the solvent is evaporated. The product is recrystallized from methanol to obtain a crushed white powder of 2-carboxy-4-hydroxy-5-methylindole (0.5 g).

Yield=61%, m.p.=262° C. Analysis: $C_{10}H_9NO_3$

|  | C | H | N | O |
|---|---|---|---|---|
| Calculated: | 62.82 | 4.74 | 7.33 | 25.11 |
| Found: | 62.85 | 4.76 | 7.28 | 25.35 |

We claim:

1. A tinctorial composition for dyeing keratinous fibers comprising in a medium suitable for dyeing said fibers at least one oxidation dyestuff precursor selected from the group consisting of a paraphenylenediamine, a para-aminophenol, a bis-phenylalkylenediamine, an ortho aminophenol and an orthophenylenediamine, in combination with at least one heterocyclic coupler having the formula

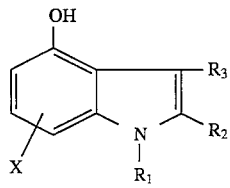

wherein $R_1$ represents hydrogen or $C_1$–$C_4$ alkyl, $R_2$ represents hydrogen, $C_1$–$C_4$ lower alkyl, carboxyl or alkoxycarbonyl, $R_3$ represents hydrogen, halogen, $C_1$–$C_4$ lower alkyl, carboxyl, alkoxycarbonyl or formyl, X represents hydrogen, $C_1$–$C_4$ alkyl, halogen, acetylamino or di($C_1$–$C_4$) alkylaminomethyl, with the proviso that at least one of X, $R_1$, $R_2$ and $R_3$ is other than hydrogen, and the salts thereof, said heterocyclic coupler being present in an amount ranging from 0.05 to 3.5 percent by weight based on the total weight of said composition, and the combined weight of said oxidation dyestuff precursor and said heterocyclic coupler ranging from 0.3 to 7 percent based on the total weight of said composition, said composition being free of any benzoquinone or naphthoquinone capable of oxidizing said heterocyclic coupler of formula I and being free of any iodide or nitrite in an amount capable of oxidizing said oxidation dyestuff precursor and the said heterocyclic coupler of formula I.

2. The tinctorial composition of claim 1 wherein said heterocyclic coupler of formula I is selected from the group consisting of 4-hydroxy-5-methylindole, 4-hydroxy-3-chloroindole, 4-hydroxy-5-dimethylaminomethylindole, 4-hydroxy-3-formyl-2-methyl-1-ethylindole, 4-hydroxy-3-formylindole, 4-hydroxy-3-formyl-2,6-dimethylindole, 4-hydroxy-3-formyl-1-methylindole, 4-hydroxy-1,5-dimethylindole, 4-hydroxy-5-methyl-2-carboxyindole, 4-hydroxy-6-methyl-3-ethoxycarbonylindole, 4-hydroxy-7-methylindole, 4-hydroxy-2,5-dimethyl-1-ethylindole, 4-hydroxy-2,6-dimethyl-1-ethylindole, 4-hydroxy-2-methyl-1-ethylindole, 4-hydroxy-3-ethylindole, 4-hydroxy-2,6-dimethylindole, 4-hydroxy-6-methylindole and 4-hydroxy-2-carboxy-5-methylindole.

3. The tinctorial composition of claim 1 wherein said paraphenylenediamine has the formula

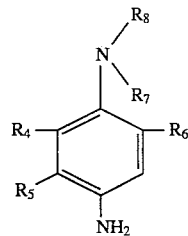

wherein $R_4$, $R_5$ and $R_6$, each independently, represent hydrogen, halogen, alkyl having 1–4 carbon atoms or alkoxy having 1–4 carbon atoms, $R_7$ and $R_8$, each independently, represent hydrogen, alkyl, hydroxyalkyl, alkoxyalkyl, carbamyl alkyl, mesyl aminoalkyl, acetylamino alkyl, ureidoalkyl, carbalkoxyaminoalkyl, piperidinoalkyl or morpholinoalkyl, wherein the alkyl and alkoxy moieties have from 1–4 carbon atoms, or $R_7$ and $R_8$, together with the nitrogen atom to which they are attached, form a piperidino or morpholino heterocycle, with the proviso that $R_4$ or $R_6$ represents hydrogen when $R_7$ and $R_8$ do not represent hydrogen, and the salts of said paraphenylenediamine.

4. The tinctorial composition of claim 3 wherein said paraphenylenediamine of formula II is selected from the group consisting of paraphenylenediamine, paratoluylenediamine, methoxyparaphenylenediamine, chloroparaphenylenediamine, 2,6-dimethylparaphenylenediamine, 2,5-dimethylparaphenylenediamine, 2-methyl-5-methoxyparaphenylenediamine, 2,6-dimethyl-5-methoxyparaphenylenediamine, N,N-dimethylparaphenylenediamine, 3-methyl-4-amino,N,N-diethylaniline, N,N-di(β-hydroxyethyl) paraphenylenediamine, 3-methyl-4-amino-N,N-di-(β-hydroxyethyl) aniline, 3-chloro-4-amino-N,N-di-(β-hydroxyethyl) aniline, 4-amino-N,N-(ethyl, carbamylmethyl) aniline, 3-methyl-4-amino-N,N-(ethyl, carbamylmethyl) aniline, 4-amino-N,N-(ethyl, β-piperidinoethyl) aniline, 3-methyl-4-amino-N,N-(ethyl, β-piperidinoethyl) aniline, 4-amino-N,N-(ethyl, β-morpholinoethyl) aniline, 3-methyl-4-amino-N,N-(ethyl, β-morpholinoethyl) aniline, 4-amino-N,N-(ethyl, β-acetylaminoethyl) aniline, 4-amino-N-(β-methoxyethyl) aniline, 3-methyl-4-amino-N,N-(ethyl, β-acetylaminoethyl) aniline, 4-amino-N,N-(ethyl, β-mesylaminoethyl) aniline, 3-methyl-4-amino-N,N-(ethyl, β-mesylaminoethyl) aniline, 4-amino-N,N-(ethyl, β-sulphoethyl) aniline, 3-methyl-4-amino-N,N-(ethyl, β-sulphoethyl) aniline, N-[(4'-amino) phenyl] morpholine, N-[(4'-amino) phenyl] piperidine and the salts thereof.

5. The tinctorial composition of claim 1 where said para aminophenol is selected from the group consisting of para aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

6. The tinctorial composition of claim 1 wherein said bis-phenylalkylenediamine has the formula

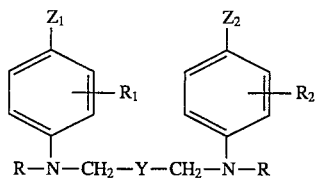

wherein $Z_1$ and $Z_2$, each independently, represent hydroxyl or $NHR_3$ wherein $R_3$ represents hydrogen or lower alkyl, $R_1$ and $R_2$, each independently, represent hydrogen, halogen or alkyl, R represents hydrogen, alkyl, hydroxyalkyl, or aminoalkyl wherein the amino moiety is substituted or unsubstituted, and Y represents a member selected from the group consisting of —$(CH_2)_n$—, —$(CH_2)_n$—O—$(CH_2)_n$—, —$(CH_2)_n$—CHOH—$(CH_2)_n$— and

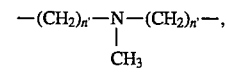

where n is an integer ranging from 0 to 8 and n' is an integer ranging from 0 to 4, and the acid addition salt of said bis-phenylalkylenediamine.

7. The tinctorial composition of claim 6 wherein said bis-phenylalkylenediamine of formula IIa is selected from the group consisting of N,N'-bis (β-hydroxyethyl)-N,N'-bis (4'-aminophenyl)-1,3-diaminopropan-2-ol, N,N'-bis (β-hydroxyethyl)-N,N'-bis(4'-aminophenyl) ethylenediamine, N,N'-bis (4-aminophenyl)-tetramethylenediamine, N,N'-bis (β-hydroxyethyl)-N,N'-bis (4-aminophenyl) tetramethylenediamine, N,N'-bis (4-methylaminophenyl) tetramethylenediamine and N,N'-bis (ethyl)-N,N'-bis (4'-amino-3'-methylphenyl) ethylenediamine.

8. The tinctorial composition of claim 1 which also contains, in addition to the heterocyclic coupler of formula (I), a metadiphenol, a meta-aminophenol, a metaphenylenediamine, a meta-acylaminophenol, a meta-ureidophenol, a metacarbalkoxyamino-phenol α-naphthol, 4-hydroxyindole, a β-ketocompound or a pyrazolone.

9. The tinctorial composition of claim 1 which also contains a direct dye.

10. The tinctorial composition of claim 1 wherein said medium suitable for dyeing said fibers is an aqueous medium having a pH ranging from 8 to 11.

11. The tinctorial composition of claim 1 which also contains an anionic, cationic, nonionic or amphoteric surfactant or a mixture thereof.

12. The tinctorial composition of claim 1 which also contains an organic solvent present in an amount ranging from 1 to 40 percent by weight based on the total weight of said composition.

13. The tinctorial composition of claim 1 which also contains one or more of a thickener, an antioxidant, a penetration agent, a sequestering agent, a buffer and a perfume.

14. The tinctorial composition of claim 1 in the form of a liquid, a cream, a gel or an aerosol packaged in the presence of a propellant.

15. A method for dyeing keratinous fibers comprising applying to said fibers in an amount sufficient to dye said fibers the said tinctorial composition of claim 1 in the presence of an oxidizing agent, leaving said composition in contact with said fibers for a period of time ranging from 10 to 40 minutes, rinsing said fibers, washing said fibers, rinsing said fibers and drying said fibers.

16. A tinctorial composition for dyeing keratinous fibers comprising in a medium suitable for dyeing said fibers at least one oxidation dyestuff precursor selected from a paraphenylenediamine, a paraaminophenol, a bis-phenylalkylenediamine, an orthoaminophenol, and an orthophenylenediamine, in combination with at least one heterocyclic coupler having the formula

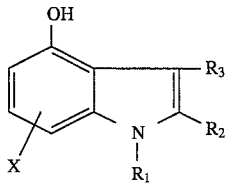 (I)

wherein $R_1$ represents hydrogen or $C_1$–$C_4$ alkyl, $R_2$ represents hydrogen or $C_1$–$C_4$ lower alkyl, $R_3$ represents hydrogen or formyl, X represents hydrogen or $C_1$–$C_4$ alkyl with the proviso that at least one of X, $R_1$, $R_2$ and $R_3$ is other than hydrogen, and the salts thereof, said heterocyclic coupler being present in an amount ranging from 0.05 to 3.5 percent by weight based on the total weight of said composition, and the combined weight of said oxidation dyestuff precursor and said heterocyclic coupler ranging from 0.3 to 7 percent based on the total weight of said composition, said composition being free of any benzoquinone or naphthoquinone capable of oxidizing said heterocyclic coupler of formula I and being free of any iodide or nitrite in an amount capable of oxidizing said oxidation dyestuff precursor and the said heterocyclic coupler of formula I.

17. The composition of claim 16 wherein said heterocyclic coupler is selected from the group consisting of 4-hydroxy-5-methylindole and 4-hydroxy-3-formylindole.

18. A method for dyeing keratinous fibers comprising in a first step applying to said fibers a first composition comprising in a medium suitable for dyeing said fibers at least one oxidation dyestuff precursor selected from the group consisting of a paraphenylenediamine, a paraaminophenol, a bis-phenylalkylenediamine, an orthoaminophenol and an orthophenylenediamine, in a second step applying to said fibers a second composition comprising in a medium suitable for dyeing said fibers a heterocyclic coupler having the formula

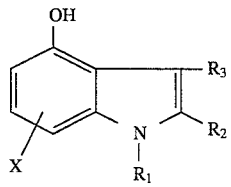 (I)

wherein $R_1$ represents hydrogen or $C_1$–$C_4$ alkyl, $R_2$ represents hydrogen, $C_1$–$C_4$ lower alkyl, carboxyl or alkoxycarbonyl, $R_3$ represents hydrogen, halogen, $C_1$–$C_4$ lower alkyl, carboxyl, alkoxycarbonyl or formyl, X represents hydrogen, $C_1$–$C_4$ alkyl, halogen, acetylamino or di($C_1$–$C_4$) alkylaminomethyl, with the proviso that at least one of X, $R_1$, $R_2$ and $R_3$ is other than hydrogen, and the salts thereof, present in an amount ranging from 0.05 to 3.5 percent by weight and introducing an oxidizing agent into said composition applied to said fibers in said second step just before application thereof to said fibers, or in a third step applying to said fibers said oxidizing agent, the combined weight of said oxidation dyestuff precursor and said heterocyclic coupler applied to said fibers ranging from 0.3 to 7 percent based on the total weight of said first and second compositions.

19. In a process for the oxidation dyeing of keratinous fibers employing a composition containing at least one oxidation dye precursor selected from the group consisting of a paraphenylenediamine, a paraaminophenol, a bis-phenylalkylenediamine, an orthoaminophenol and an orthophenylenediamine in combination with a coupler, the improvement comprising, as said coupler for said oxidation dyeing of said keratinous fibers, a heterocyclic coupler having the formula

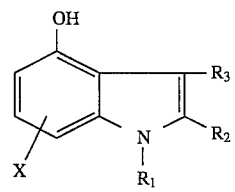 (I)

wherein $R_1$ represents hydrogen or $C_1$–$C_4$ alkyl, $R_2$ represents hydrogen, $C_1$–$C_4$ lower alkyl, carboxyl or alkoxycarbonyl, $R_3$ represents hydrogen, halogen, $C_1$–$C_4$ lower alkyl, carboxyl, alkoxycarbonyl or formyl, X represents hydrogen, $C_1$–$C_4$ alkyl, halogen, acetylamino or di($C_1$–$C_4$) alkylaminomethyl, with the proviso that at least one of X, $R_1$, $R_2$ and $R_3$ is other than hydrogen, and the salts thereof, present in an amount ranging from 0.05 to 3.5 percent by weight, and the combined weight of said oxidation dye precursor and said heterocyclic coupler used in said process ranging from 0.3 to 7 percent by weight of said composition.

20. A method for dyeing keratinous fibers comprising in a first step applying to said fibers a first composition comprising in a medium suitable for dyeing said fibers at least one oxidation dyestuff precursor selected from the group consisting of a paraphenylenediamine, a paraaminophenol, a bis-phenylalkylenediamine, an orthoaminophenol and an orthophenylenediamine, in a second step applying to said fibers a second composition comprising in a medium suitable for dyeing said fibers, a heterocyclic coupler having the formula

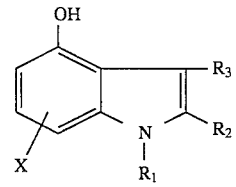 (I)

wherein

R₁ represents hydrogen or $C_1$–$C_4$ alkyl,

R₂ represents hydrogen or $C_1$–$C_4$ lower alkyl,

R₃ represents hydrogen or formyl,

X represents hydrogen or $C_1$–$C_4$ alkyl with the proviso that at least one of X, $R_1$, $R_2$ and $R_3$ is other than hydrogen, and the salts thereof, present in an amount ranging from 0.05 to 3.5 percent by weight and introducing an oxidizing agent into said composition applied to said fibers in said second step just before application thereof to said fibers, or in a third step applying to said fibers said oxidizing agent, the combined weight of said oxidation dyestuff precursor and said heterocyclic coupler applied to said fibers ranging from 0.3 to 7 percent based on the total weight of said first and second compositions.

21. In a process for the oxidation dyeing of keratinous fibers employing a composition containing at least one oxidation dye precursor selected from the group consisting of a paraphenylenediamine, a paraaminophenol, a bis-phenylalkylenediamine, an orthoaminophenol and an orthophenylenediamine in combination with a coupler, the improvement comprising, as said coupler for said oxidation dyeing of said keratinous fibers, a heterocyclic coupler having the formula

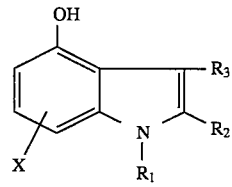

(I)

wherein

R₁ represents hydrogen or $C_1$–$C_4$ alkyl,

R₂ represents hydrogen or $C_1$–$C_4$ lower alkyl,

R₃ represents hydrogen or formyl,

X represents hydrogen or $C_1$–$C_4$ alkyl with the proviso that at least one of X, $R_1$, $R_2$ and $R_3$ is other than hydrogen, and the salts thereof, present in an amount ranging from 0.05 to 3.5 percent by weight, and the combined weight of said oxidation dye precursor and said heterocyclic coupler used in said process ranging from 0.3 to 7 percent by weight of said composition.

* * * * *